United States Patent [19]
Strandberg et al.

[11] Patent Number: 6,149,663
[45] Date of Patent: Nov. 21, 2000

[54] GUIDE WIRE BRAKE FOR ABLATION ASSEMBLY

[75] Inventors: Roy T. Strandberg, Sacramento, Calif.; Thomas J. Hiblar, Everett, Wash.

[73] Assignee: Scimed Life Systems, Inc., Maple Grove, Minn.

[21] Appl. No.: 09/376,739

[22] Filed: Aug. 17, 1999

[51] Int. Cl.$^7$ .................................................. A61B 17/00
[52] U.S. Cl. .................... 606/180; 606/159; 606/170; 600/581
[58] Field of Search ................................ 606/1, 108, 159, 606/170, 171, 180; 604/96–100; 600/581

[56] References Cited

U.S. PATENT DOCUMENTS

| | | |
|---|---|---|
| 4,679,557 | 7/1987 | Opie et al. . |
| 4,926,858 | 5/1990 | Gifford, III et al. . |
| 5,011,490 | 4/1991 | Fischell et al. . |
| 5,314,407 | 5/1994 | Auth et al. . |
| 5,490,859 | 2/1996 | Mische et al. . |
| 5,501,694 | 3/1996 | Ressemann et al. . |
| 5,584,843 | 12/1996 | Wulfman et al. . |
| 5,667,490 | 9/1997 | Keith et al. . |
| 5,779,722 | 7/1998 | Shturman et al. . |
| 5,893,857 | 4/1999 | Shturman et al. . |

*Primary Examiner*—Michael Buiz
*Assistant Examiner*—William Lewis
*Attorney, Agent, or Firm*—Christensen O'Connor Johnson Kindness PLLC

[57] ABSTRACT

A guide wire brake for use in an ablation assembly includes a clamp positioned in and between recesses provided in an air-actuated piston and a retainer. The clamp is provided with a first member and a second member coupled together on opposite sides of a spring member. An outer surface of the clamp is tapered to matingly engage the tapered inner surface of the first and second recesses. In operation, the piston is in fluid communication with a source of air. As air contacts an inner surface of the piston, the piston moves toward the retainer, thereby pushing the first and second recesses together along the tapered outer surface of the clamp. This action causes the first and second members to overcome the spring force of the spring member, and clamp together against a guide wire extending therethrough, thereby preventing longitudinal and rotational motion of the guide wire. The first member has two studs that extend through apertures provided in the second member, and a crescent washer is provided around each of the studs, to function as a spring.

10 Claims, 6 Drawing Sheets

GUIDE WIRE BRAKE FOR ABLATION ASSEMBLY

FIELD OF THE INVENTION

This invention relates to an apparatus for ablating unwanted material from the patient's vasculature, and more particularly, to a guide wire brake for use in an ablation assembly.

BACKGROUND OF THE INVENTION

Vascular diseases, such as atherosclerosis and the like, have become quite prevalent in the modern day. These diseases may manifest themselves in a number of ways, often requiring different forms or methods of treatment for curing the adverse effects of the diseases. For example, vascular diseases may take the form of deposits or growths in a patient's vasculature which may restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies have been developed. For example, treatment devices have been developed that remove the material occluding a vascular lumen. Such treatment devices, sometimes referred to as atherectomy devices or ablation assemblies, use a variety of material removal devices, such as rotating cutters or ablaters for example, to remove the occluding material. (The term "atherectomy device" as used in the specification refers to a device for removing an occlusion in any portion of a patient's vasculature. Thus, while the atherectomy devices provided in accordance with preferred embodiments of the present invention are well suited for use in the coronary arteries, their use is not limited to the coronary arteries.) The material removal device, such as a rotatable burr, is typically rotated via a driveshaft that extends out of the vasculature of the patient and to an electric motor or turbine which is typically powered by a fluid such as air.

In operation, a material removal device secured to the distal end of a driveshaft is typically advanced over a guide wire placed in vivo until the material removal device is positioned just proximal to the occluded site. A drive assembly having a motor or turbine is used to rotate the driveshaft and the material removal device while the material removal device is moved through the occluded vessel. The material removal device engages the occluding material and removes the material from the vessel, rather than merely displacing or reforming the material as in a balloon angioplasty procedure.

An example of a currently available ablation assembly is the Rotablator® atherectomy system, manufactured by Boston Scientific. In this system, a main advancer housing encloses the drive assembly and a guide wire brake. An ablation device, such as a burr, and a rotatable driveshaft, are coupled to the drive assembly in the advancer housing, such that torque from the drive assembly is transmitted to the driveshaft, and the burr is advanced and retracted via longitudinal motion of the drive assembly.

As discussed above, the ablation device is typically advanced over a guide wire. The guide wire extends longitudinally through the entire ablation assembly, including the guide wire brake, drive assembly, driveshaft and ablation device. In operation, once the guide wire and ablation device are positioned within the patient's vasculature at a desired location, it is desirable to clamp the guide wire with the guide wire brake to prevent any longitudinal or rotational movement of the guide wire, prior to activating the drive assembly.

In the guide wire brake assembly currently manufactured by Boston Scientific, a collet having a passageway extending therethrough is positioned between an air-actuated piston and a brake retainer. Prior to activating a turbine of the drive assembly, air is provided to the piston, causing it to move toward the retainer against an end of the collet. The pressure of the piston against the end of the collet causes the collet to close around the guide wire, thereby preventing longitudinal and rotational movement of the guide wire. Although such a conventional brake assembly provides acceptable results, it is relatively expensive to manufacture and it can be difficult to thread the guide wire through the brake. It would therefore be desirable to provide a guide wire brake for an ablation assembly that provides good control of the guide wire, while simplifying use and reducing manufacturing costs. The present invention fulfills these needs, and provides further related advantages.

SUMMARY OF THE INVENTION

Briefly, the present invention provides an ablation assembly having a guide wire brake that restrains motion of a guide wire both longitudinally and rotationally. In a preferred embodiment, the guide wire brake is positioned within a housing, that also contains a drive assembly coupled to a driveshaft, which in turn is coupled to an ablation device. The drive assembly transmits torque and longitudinal motion to the driveshaft and ablation device. A guide wire extends longitudinally through the assembly, namely, through the guide wire brake assembly, drive assembly, driveshaft and ablation device.

In a preferred embodiment, the guide wire brake assembly is provided with a piston having a first recess extending inward from an outer surface of the piston. A retainer is spaced longitudinally from the piston, and has a second recess aligned with the first recess in the piston. Both the first and second recesses are tapered. A clamp is positioned in and between the first and second recesses, an outer surface of the clamp being tapered by the same angle of the first and second recesses to matingly engage the first and second recesses. The clamp has a first member and a second member coupled together on opposite sides of a spring member. A spring force from the spring member spaces the first and second members apart from each other sufficiently to allow the guide wire to extend and be moved freely between the first and second members. Although the first and second members may be formed in a variety of ways, in a preferred embodiment, the first member has two studs extending outward from an inner surface through two corresponding apertures provided in the second member. A spring or crescent washer is provided around each stud.

In operation, fluid, such as air, is allowed to flow against an inner surface of the piston, causing the piston to move toward the retainer. The movement of the piston towards the retainer forces the first and second members together against the guide wire, thereby preventing movement of the guide wire. Air is then fed to the turbine of the drive assembly, to begin rotation of the ablation device. Once the ablation is completed, the flow of air is stopped, thereby causing the turbine to spin down and the pressure on the inner surface of the piston to be released. The piston moves away from the retainer, thereby allowing the first and second members of the clamp to separate due to the spring member. The guide wire is then again free to move longitudinally and rotationally.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE INVENTION

Figure 1:
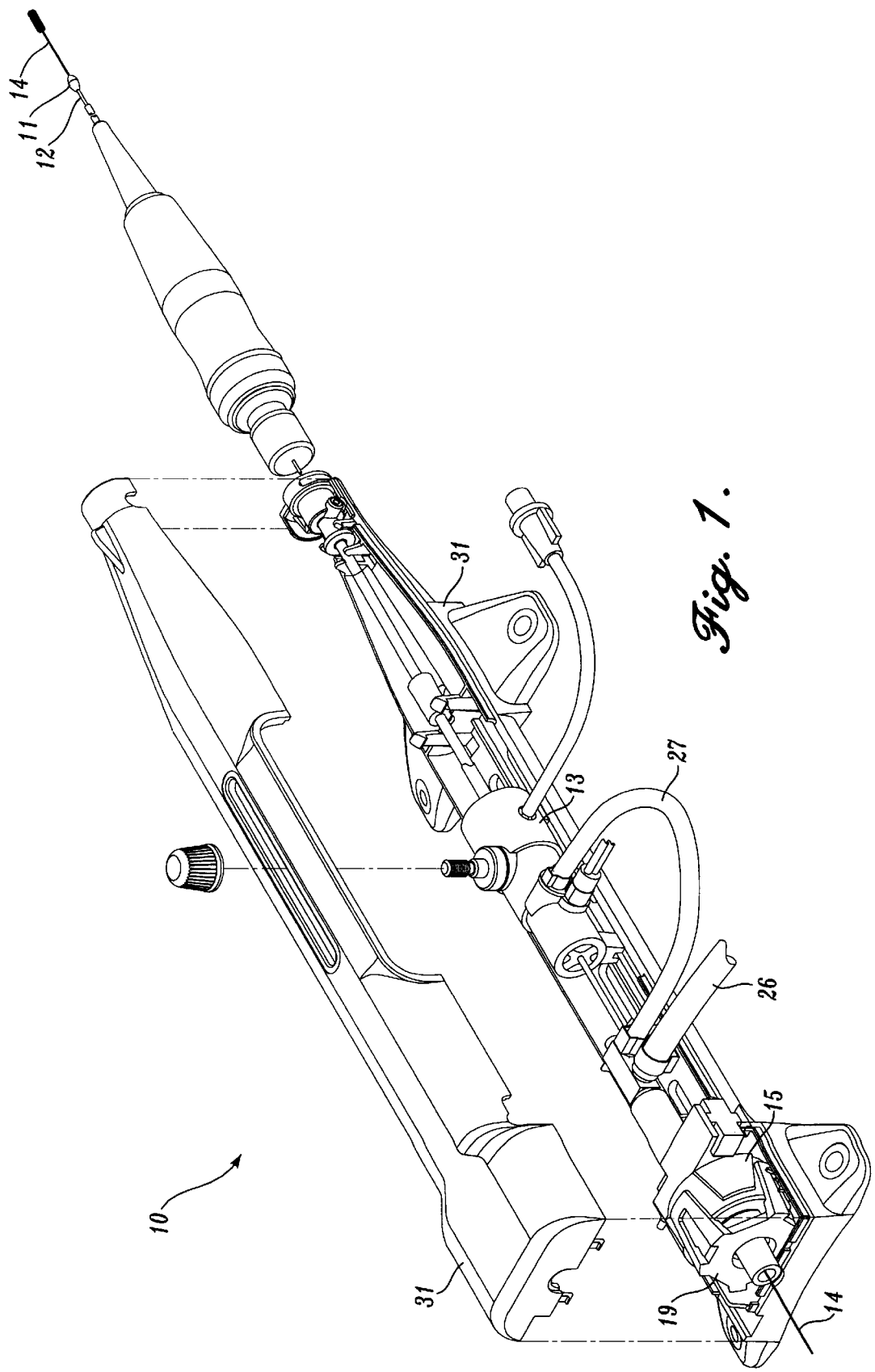
FIG. 1 is a partially exploded isometric view of an ablation assembly provided in accordance with a preferred embodiment of the present invention.

An ablation assembly 10 provided in accordance with a preferred embodiment of the present invention is illustrated in FIG. 1. The ablation assembly 10 includes an ablation device 11, such as a rotatable burr, coupled to the distal end of a driveshaft 12. The driveshaft is coupled to a drive assembly 13 positioned within an advancer housing 31. The drive assembly includes an air-driven turbine (not shown) that transmits torque to the driveshaft and ablation device. Also, given the coupling of the driveshaft 12 to the drive assembly 13, longitudinal motion of the drive assembly 13 along the length of the advancer housing 31 is transmitted to the ablation device 11, to selectively advance and retract the ablation device through a lesion in a patient's vasculature.

As discussed previously, the ablation assembly is positioned in a patient's vasculature over a guide wire 14, that extends longitudinally through the ablation assembly 10. To control the movement of the guide wire, the advancer housing includes a brake assembly 15 through which the guide wire 14 passes.

Figure 2:
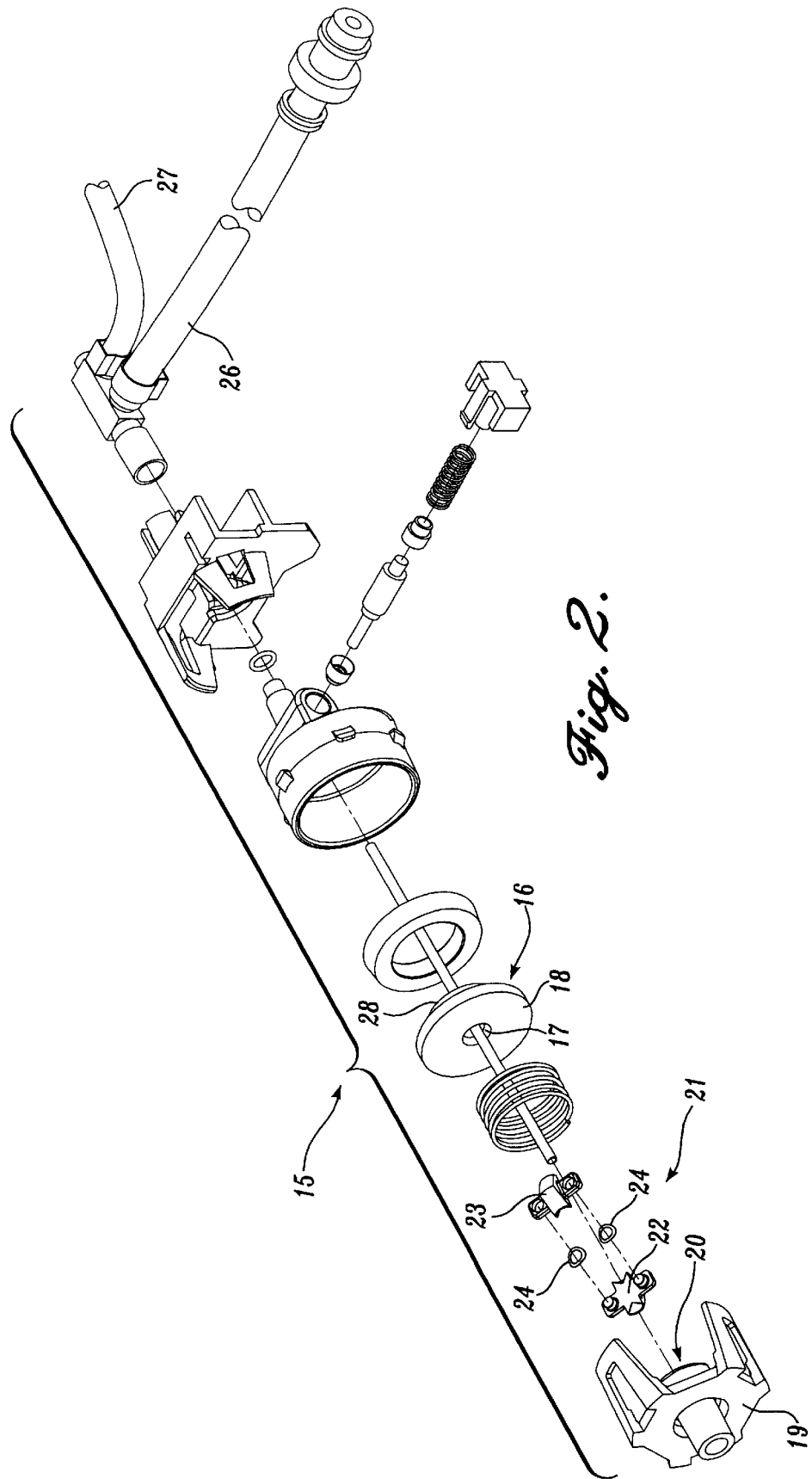
FIG. 2 is an exploded isometric view of a brake assembly forming a part of the ablation assembly illustrated in FIG. 1.
Figure 5:
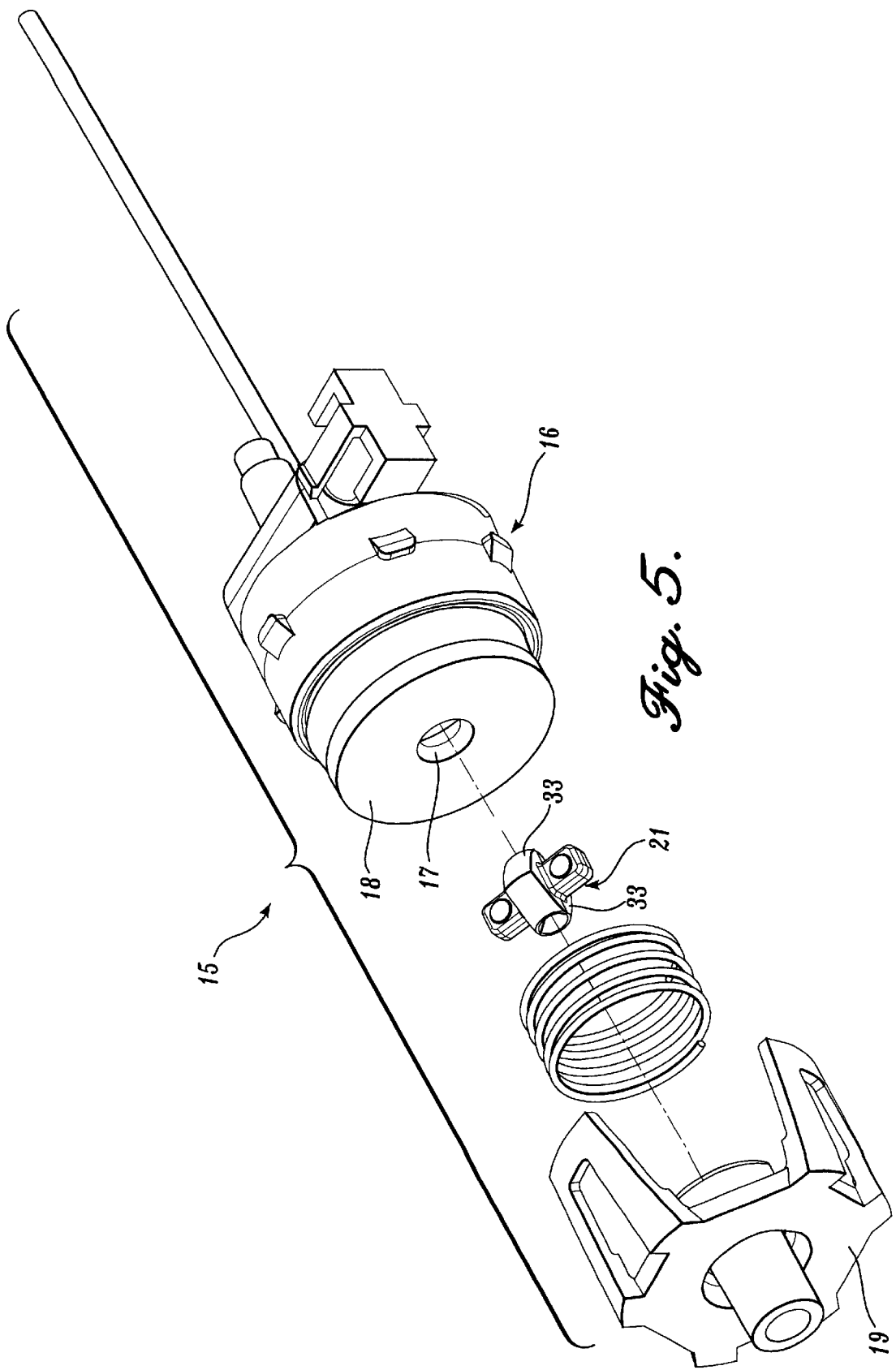
FIG. 5 is an isometric partially assembled view of the brake assembly shown in FIG. 2.
Figure 6:
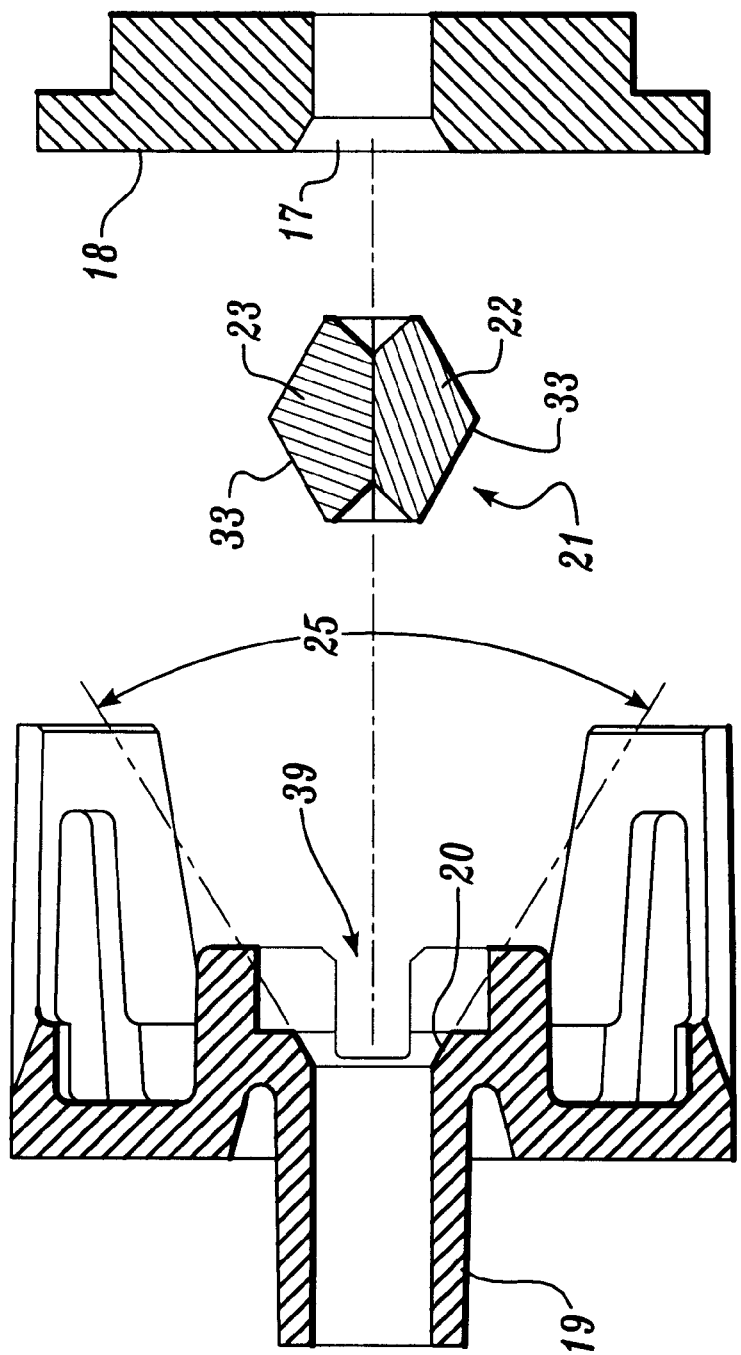
FIG. 6 is a cross-sectional elevation view of a brake retainer forming a portion of the brake assembly of FIGS. 2 and 5.

In a preferred embodiment, the brake assembly 15 includes a piston 16 in fluid communication with a source of fluid, such as air (not shown). As illustrated in FIGS. 1 and 2, a first conduit 26 allows air to flow from the source of fluid to the piston and a second conduit 27 allows air to subsequently flow to the drive assembly 13. As best seen in FIGS. 2, 5, and 6, a first recess 17 is provided in an outer surface or proximal face 18 of piston 16. A retainer 19 is spaced longitudinally from the piston, and has a second recess 20 aligned with the first recess 17 of the piston. In a preferred embodiment, both the first and second recesses are tapered. Although a variety of tapered angles may be used, in a preferred embodiment, the included angle of taper 25 for each of the first and second recesses is 30°–90°, and preferably 60°, as shown in FIG. 6.

Figure 3:
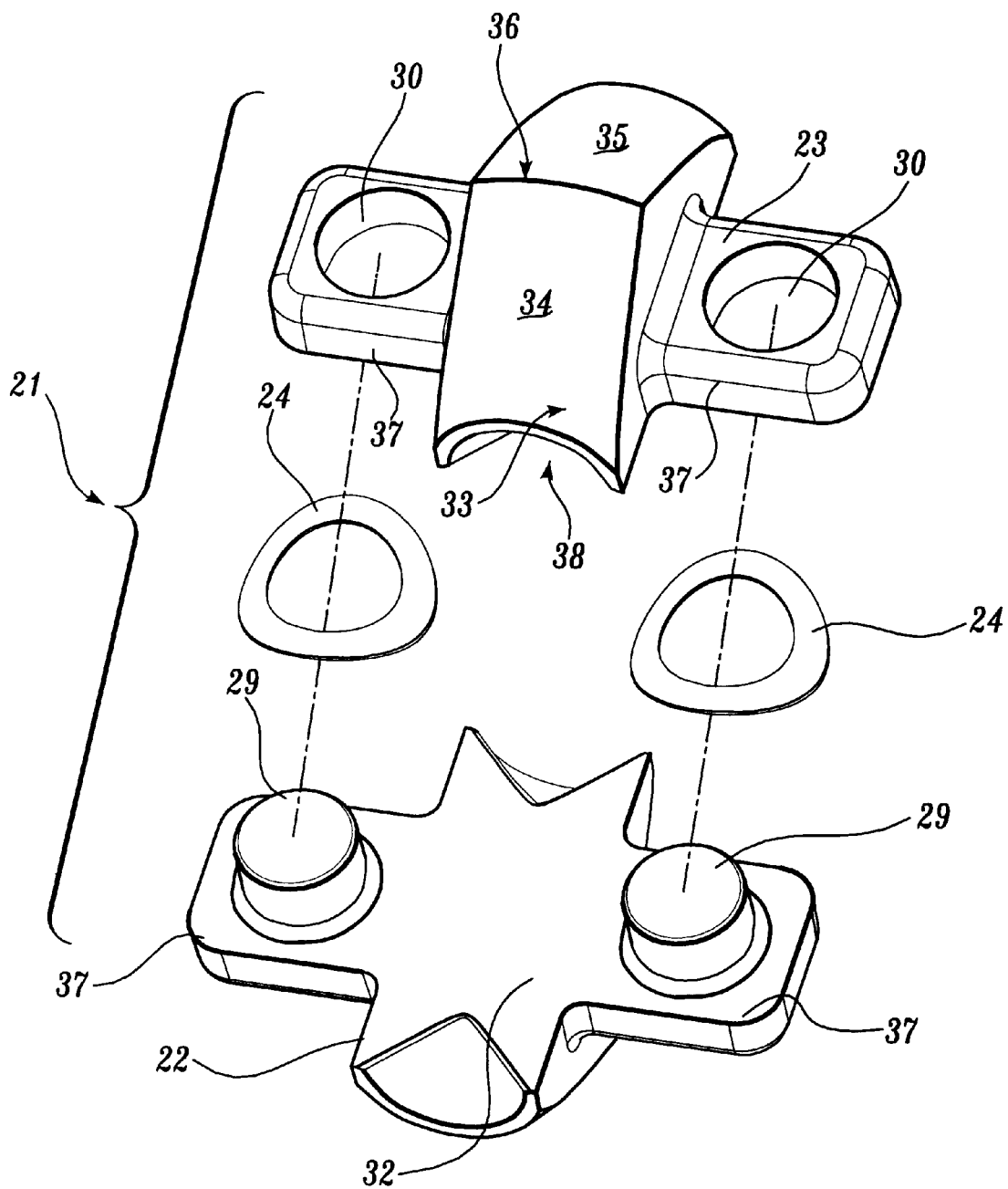
FIG. 3 is an enlarged, exploded view of a clamp forming a part of the brake assembly illustrated in FIG. 2.

A clamp 21 is positioned in and between the first recess 17 and second recess 20. In a preferred embodiment, the clamp 21 includes a first member 22 and a second member 23 coupled together on opposite sides of a spring member 24. In a preferred embodiment, as best seen in FIG. 3, the first and second members 22, 23 form two halves of the clamp 21. Each half includes a generally flat surface 32 where the two halves abut. The outer surface 33 of each of the first and second members includes a sloping forward surface 34 and a sloping rear surface 35. The sloping surfaces 34, 35 meet in the middle of each half, to form a peak 36. The sloping outer surfaces 33 of the clamp are designed to mate with the tapered recesses 17, 20 in the piston 16 and the retainer 19. To align the top and bottom halves of the clamp, each half includes a pair of tabs 37 that extend laterally outward from a central region 38 of the clamp. Each of the tabs 37 on the first member 22 include a post or stud 29 that fits within an aperture 30 on the corresponding tab of the second member 23. Positioned over each of the studs 29 is a spring washer 24 that biases the first member 22 and second member 23 away from each other.

When the brake assembly 15 is at rest, a spring force from spring member 24 causes the first and second members to be spaced apart sufficiently to allow guide wire 14 to extend and be moved freely between the first and second members. When it is desired to use the ablation assembly, the operator activates the system, for example, by depressing a foot pedal (not shown). Air is provided from the source of air through the first conduit 26 to act against an inner surface 28 of piston 16. The force of the air pressure against the piston causes the piston to move toward the retainer 19, thereby forcing the tapered surfaces of the first and second members further into the first and second recesses, respectively. The movement of the piston toward the retainer 19 therefore causes the first and second members to overcome the spring force of spring member 24, thereby clamping together against the guide wire 14. In this manner, longitudinal and rotational motion of the guide wire is prevented. Air then flows from the first conduit 26 to the second conduit 27 to activate the drive assembly 13, which in turn activates the ablation device 11. Once the ablation is complete, an operator deactivates the system, for example, by releasing a foot pedal, thereby ceasing the flow of air to the conduits. The drive assembly 13 winds down, and the piston 16 retracts away from retainer 19, such that spring member 24 once again causes first member 22 and second member 23 to separate, allowing free movement of guide wire 14.

In a preferred embodiment, the retainer 19 is further provided with a slot 39, as best seen in FIG. 6. The slot 39 maintains the proper alignment of the first and second members 22, 23 of clamp 21 while the brake is disengaged, namely when clamp 21 is not engaged by piston 16. The slot 39 is sufficiently wide to accommodate both the first and second members 22, 23 and the wave washers 24 with a small amount of compression preload. As a result, clamp 21 is prevented from disassembling when the brake is deactivated. Slot 39 also constrains the clamp 21 so there is an appropriate distance between the first and second members 22, 23, preferably 0.010–0.020 inch, thereby making it possible for the piston 16 to engage the sloping outer surfaces 33 of the clamp 21. Finally, the slot 39 aids in assembly, given that the clamp 21 is simply dropped into the slot during the assembly process.

Figure 4:
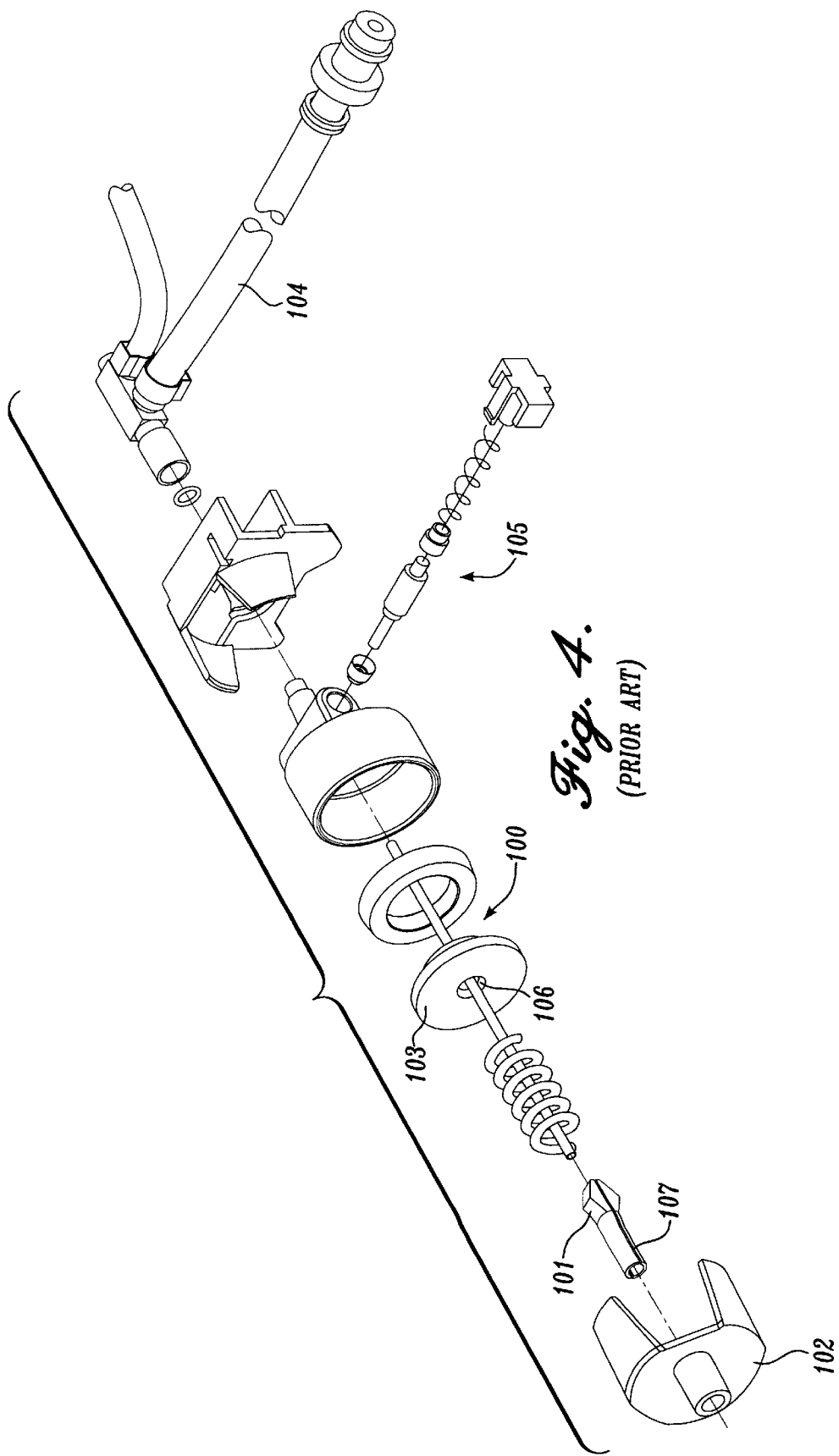
FIG. 4 is an exploded isometric view of a prior art brake assembly.

A prior art brake assembly is illustrated in FIG. 4. Such a prior art brake assembly 100 may be found, for example, in the Rotablator® atherectomy system manufactured by Boston Scientific. In the prior art brake assembly 100, a collet 101 is positioned between a retainer 102 and a piston 103 which is fluidly coupled to conduit 104, which in turn is coupled to a supply of fluid, for example, air. A longitudinal passageway 107 extends through the length of the collet 101 and a guide wire extends therethrough. When the piston is actuated, a distal end of collet 101 is forced into recess 106 of piston 103, thereby compressing the collet. A defeat mechanism 105 is provided in the prior art system, which when actuated, prevents the flow of air to the piston, thereby releasing the brake. A brake assembly provided in accordance with the present invention is more simple to use than the prior art device because the guide wire does not have to be threaded through the long, slotted tube of a collet, which occasionally causes the guide wire to catch and/or be misdirected. The present invention also provides a brake assembly that is more economical to manufacture.

From the foregoing, it will be appreciated that although embodiments of the invention have been described herein for purposes of illustration, various modifications may be made without deviating from the spirit of the invention. Thus, the present invention is not limited to the embodiments described herein, but rather is defined by the claims which follow.

The embodiments of the invention in which an exclusive property or privilege is claimed are defined as follows:

1. An ablation assembly comprising:
  an ablation device coupled to a driveshaft and to a drive assembly, the drive assembly transmitting torque and longitudinal motion to the driveshaft and ablation device; and
  a brake assembly provided with a piston having a first recess extending inwardly from an outer surface of the piston, a retainer having a second recess aligned with the first recess, and a clamp positioned in and between the first and second recesses, the clamp having a first member, a second member and a spring member, the first and second members being coupled together on opposite sides of the spring member, the first and second members being spaced apart by a spring force provided by the spring member sufficiently to allow a guide wire to extend and be moved freely between the first and second members, the first and second members overcoming the spring force and clamping together by movement of the piston towards the retainer, to prevent movement of the guide wire.

2. The ablation assembly according to claim 1, wherein the first and second recesses are tapered, and the first and second members are tapered to matingly engage the first and second recesses.

3. The ablation assembly according to claim 1, wherein the piston is fluidly coupled to a source of air and is selectively moved toward the retainer by allowing air to flow from the source of air against an inner surface of the piston.

4. The ablation assembly according to claim 1, wherein the first member has a plurality of studs extending outward from an inner surface through a corresponding plurality of apertures provided in the second member.

5. The ablation assembly accordingly to claim 4, wherein the spring element further comprises a crescent washer provided around each stud.

6. An ablation assembly comprising:
  an ablation device coupled to a driveshaft and to a drive assembly, the drive assembly transmitting torque and longitudinal motion to the driveshaft and ablation device;
  a brake assembly having a clamp provided with a first member and a second member coupled together on opposite sides of a spring member, the first and second members being spaced apart by the spring member sufficiently to allow a guide wire to extend and be moved freely between the first and second members; and
  means for selectively pushing the first and second members together to clamp against the guide wire, thereby preventing movement of the guide wire.

7. The ablation assembly according to claim 6, wherein the first member has a plurality of studs extending outward from an inner surface through a corresponding plurality of apertures provided in the second member.

8. The ablation assembly accordingly to claim 7, wherein the spring element further comprises a crescent washer provided around each stud.

9. An ablation assembly comprising:
  an ablation device coupled to a driveshaft and to a drive assembly, the drive assembly transmitting torque and longitudinal motion to the driveshaft and ablation device;
  a brake assembly provided with a piston having a first tapered recess extending inward from an outer surface of the piston, a retainer having a second tapered recess aligned with the first recess, the piston being coupled to a source of fluid and being selectively moved toward the retainer by allowing fluid to flow from the source of fluid against an inner surface of the piston, and a clamp positioned in and between the first and second recesses, the clamp having a first member, a second member and a spring member, the first and second members being coupled together on opposite sides of the spring member, an outer surface of each of the first and second members being tapered to matingly engage the first and second recesses, the first member having a plurality of studs extending outward from an inner surface through a corresponding plurality of apertures provided in the second member, the first and second members being spaced apart by the spring member sufficiently to allow a guide wire to extend and move freely between the first and second members, the first and second members being compressed together by movement of the piston toward the retainer, the first and second members clamping together against the guide wire to prevent movement of the guide wire.

10. The ablation assembly according to claim 9, wherein the spring element further comprises a crescent washer provided around each stud.

* * * * *

UNITED STATES PATENT AND TRADEMARK OFFICE
CERTIFICATE OF CORRECTION

PATENT NO.    : 6,149,663
DATED         : November 21, 2000
INVENTOR(S)   : R.T. Strandberg et al.

It is certified that error appears in the above-identified patent and that said Letters Patent is hereby corrected as shown below:

<u>Title page,</u>
Item [75], Inventors, after "Wash." insert -- ; Stephen L. McKelvy, Bellevue, Wash. --

Signed and Sealed this

Twenty-fifth Day of March, 2003

JAMES E. ROGAN
*Director of the United States Patent and Trademark Office*